United States Patent [19]

Cragoe, Jr. et al.

[11] 4,249,021

[45] Feb. 3, 1981

[54] INDANACETIC ACID COMPOUNDS

[75] Inventors: Edward J. Cragoe, Jr., Lansdale, Pa.; Haydn W. R. Williams, Dollard des Ormeaux, Canada; Otto W. Woltersdorf, Jr., Chalfont, Pa.

[73] Assignee: Merck & Co., Inc., Rahway, N.J.

[21] Appl. No.: 15,095

[22] Filed: Feb. 26, 1979

[51] Int. Cl.³ ............................................. C07C 59/88
[52] U.S. Cl. ........................... 562/462; 260/326.5 C; 260/456 F; 260/465 D; 260/501.16; 424/248.54; 424/267; 424/269; 424/274; 424/304; 424/308; 424/309; 424/316; 424/317; 424/319; 424/324; 544/176; 546/206; 548/253; 560/47; 560/48; 560/51; 560/53; 560/54; 562/456; 562/457; 564/169

[58] Field of Search ...................... 562/462, 456, 457; 260/558 A, 558 R, 559 R, 465 D; 560/47, 48, 51, 53; 424/316, 317, 319, 308, 309, 304, 324

[56] References Cited

U.S. PATENT DOCUMENTS

| 3,929,872 | 12/1975 | Cragoe, Jr. et al. | 562/462 |
| 3,984,465 | 10/1976 | Cragoe, Jr. et al. | 562/462 |
| 4,096,267 | 6/1978 | Cragoe, Jr. et al. | 562/462 |

*Primary Examiner*—Vivian Garner
*Attorney, Agent, or Firm*—Michael C. Sudol, Jr.; Harry E. Westlake

[57] ABSTRACT

Substituted 1-oxo-2,2-disubstituted-5-indanacetic acids and their salts, esters and amides are disclosed. The products display a dual pharmaceutical utility in that they exhibit diuretic, saluretic and uricosuric activity.

2 Claims, No Drawings

INDANACETIC ACID COMPOUNDS

DESCRIPTION OF THE INVENTION

This invention relates to a new class of chemical compounds which can be described generally as substituted 1-oxo-2,2-distributed-5-indanacetic acids and to the non-toxic, pharmacologically acceptable salt, ester, and amide derivatives thereof. This invention also relates to methods for the preparation of said substituted 1-oxo-2,2-disubstituted-5-indanacetic acids and salts, esters and amides thereof. Pharmacological studies show that the instant products are effective diuretic and saluretic agents which can be used in the treatment of conditions associated with electrolyte and fluid retention, such as edema. The instant products are also useful in the treatment of hypertension. In addition, these compounds are able to maintain the uric acid concentration in the body at pretreatment levels or even effect a decrease in the uric acid concentration.

When administered in therapeutic dosages in conventional vehicles, the instant products effectively reduce the amount of sodium and chloride ions in the body, lower dangerous excesses of fluid levels to acceptable levels and, in general alleviate conditions associated with edema. In addition, these compounds overcome a major problem associated with many of the presently available diuretics and saluretics. Many of the presently available diuretics and saluretics have a tendency to induce hyperuricemia which may precipitate uric acid or sodium urate, or both, in the body which may induce from mild to severe episodes of gout. The instant compounds of this invention now provide an effective tool to treat those patients requiring diuretic and saluretic treatment without incurring the risk of inducing gout.

The substituted 1-oxo-2,2-disubstituted-5-indanacetic acids (I) of this invention have the following structural formula:

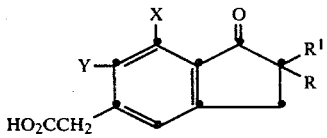

wherein

R is lower alkyl, cycloalkyl, phenyl or substituted phenyl, wherein the substituents are halogen, lower alkyl, cycloalkyl, lower alkoxy, hydroxy, amino, and cyano;

$R^1$ is lower alkyl,

X is chloro or methyl;

Y is hydrogen, chloro or methyl; pharmaceutically acceptable salts thereof and the ester and amide derivatives thereof.

The term "lower alkyl" when employed herein is deemed to include both straight and branched chain alkyl groups of from 1 to 6 carbon atoms such as methyl, ethyl, propyl, isopropyl, tert butyl, pentyl, and hexyl. The term "lower alkoxy" is deemed to include the alkoxy group, both straight and branched chain, which contain from 1 to 6 carbon atoms such as methoxy, ethoxy, propoxy, butoxy, isopentoxy, dimethyl butoxy, and the like. The term "cycloalkyl" includes saturated carbocyclic rings of from 4 to 6 carbon atoms.

The preferred embodiments of this invention are those compounds of Formula I wherein X and Y are both chloro;

$R^1$ is lower alkyl;

R is cycloalkyl or phenyl, and the pharmaceutically acceptable salts thereof.

The compounds of this invention, namely those of Formula (I) are prepared according to the following equation:

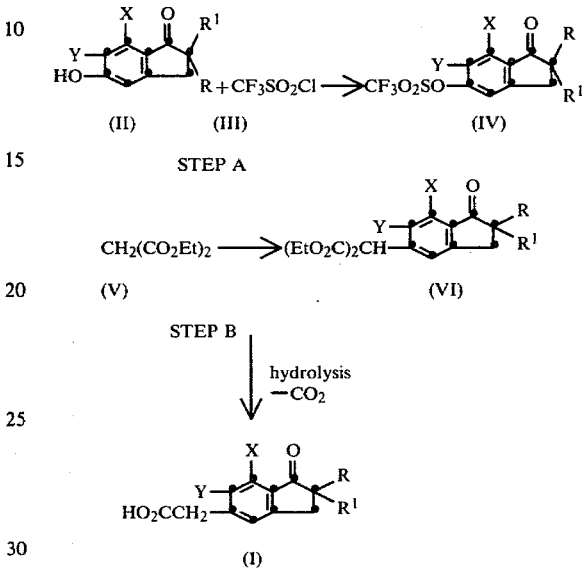

wherein X, Y, R and $R^1$ are as previously described.

In Step A, the indanone (II) is reacted with trifluoromethanesulfonyl chloride to yield a 5-trifluoromethylsulfonyloxy compound (IV). This is followed by reacting the product (IV) with a lower alkyl di-ester such as diethylmalonate to yield an intermediate indanylmalonate which is followed by the hydrolysis to yield compounds of Formula (I). In Step A, the reaction between the compounds of Formula II with the trifluoromethyl sulfonyl chloride is carried out briefly in an unreactive solvent such as for example, acetone, methylethylketone or dimethylformamide at a temperature of from about 0°–50° C. with room temperature being preferred. A base such as potassium carbonate or sodium carbonate is added. The reaction is carried out to completion to yield compounds of Formula (IV) which can be isolated by methods known in the art, such as by filtering off unwanted precipitates, extracting the product from the filtrate and triturating with an organic solvent to obtain the compounds of Formula (IV).

In Step B, the compounds of Formula (IV) are reacted with a lower alkyl di-ester such as, for example, diethyl malonate in a reaction medium such as in a solution of sodium hydride in benzene or dimethylformamide or a solution of potassium t-butoxide in t-butanol to yield the indanylmalonate compound (VI) which is not isolated but which is subject to a hydrolysis preferably an acidic hydrolysis which entails treating the intermediate indanylmalonate (VI) with a strong acid such as hydrochloric acid to yield compounds of Formula I. The products of Formula I can be isolated from the reaction mixture by merely filtering them from the reaction. A detailed preparation of the compounds of this procedure are shown in the examples. The starting materials (Formula II) are all known in the art and are described in U.S. Pat. Nos. 3,984,465 and 4,096,267.

The ester derivatives of the compounds of Formula I may be prepared by the reaction thereof with an alcohol, for example a lower alkanol. The amide derivatives may be prepared by converting a compound of Formula I to its corresponding acid halide, preferably the acid chloride, by reaction with, for example, thionyl chloride, followed by treating said acid halide with ammonia, an appropriate mono-lower alkyl amine, di-lower alkyl amine, heterocyclic substituted amine such as aminotetrazole, or a heterocyclic amine such as piperidine, morpholine, pyrrolidine, and the like, to produce the corresponding amide compound.

The pharmaceutically acceptable salts are preferably the metal salts and are prepared by treating said acid with an alkali metal or alkaline earth metal hydroxide, alkoxide, or hydride such as sodium hydroxide, potassium hydroxide, sodium methoxide, calcium hydride and the like.

These and other equivalent methods for the preparation of the ester and the amide derivatives of the instant products will be apparent to one having ordinary skill in the art and to the extent that said derivatives are both non-toxic and physiologically acceptable to the body system, said derivatives are the functional equivalents of the corresponding substituted 1-oxo-2,2-disubstituted-5-indanacetic acids.

The novel compounds of this invention are diuretic and saluretic agents. In addition, these compounds are also able to maintain the uric acid concentration within the normal limits. The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250, and 500 milligrams of the active ingredient for the symptomatic adjustment of the dosage to the patient to be treated. The total daily dose of the active ingredient will generally be from 5 mg. to 2000 mg. These dosages are well below the toxic or lethal dose of the products.

A suitable unit dosage form of the products of this invention can be administered by mixing 100 milligrams of a substituted 1-oxo-2,2-disubstituted-5-indanacetic acid (I) or a suitable salt, ester or amide derivative thereof, with 99 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods, and if desired, can be made up as elixirs or as injectable solutions by methods well known to pharmacists. An effective amount of the drug is ordinarily supplied at a dosage level of from about 1 mg. to about 50 mg/kg. of body weight. Preferably the range is from about 1 mg. to 7 mg/kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following examples are included to illustrate the preparation of compounds of this invention and also to illustrate the preparation of a representative dosage form:

EXAMPLE 1

(6,7-Dichloro-1-oxo-2-methyl-2-phenyl-5-indanyl)acetic acid

Step A: 6,7-Dichloro-2-methyl-2-phenyl-5-trifluoromethylsulfonyloxy-1-indanone

To a stirred solution of 6,7-dichloro-5-hydroxy-2-methyl-2-phenyl-1-indanone (12.28 g., 0.04 mole) in acetone (150 ml.) is added potassium carbonate (13.18 g., 0.095 mole).

After ten minutes a solution of trifluoromethanesulfonyl chloride (11.84 g., 0.07 mole) in acetone (150 ml.) is added over 10 minutes. After 15 minutes of stirring the precipitated salts are filtered and the acetone is evaporated at reduced pressure to leave an oil which upon trituration with hexane gives 15 g. of (6,7-dichloro-1-oxo-2-methyl-2-phenyl-5-indanyl)acetic acid which melts at 105°–107° C.

Elemental analysis for $C_{11}H_{11}Cl_2F_3O_4S$: Calc: C, 46.48; H, 2.52; Found: C, 46.72; H, 2.72.

Step B: (6,7-Dichloro-1-oxo-2-methyl-2-phenyl-5-indanyl)acetic acid

To a stirred suspension of sodium hydride (1.43 g., 0.06 mole) in 50% benzene-dimethylformamide (25 ml.) cooled in ice is added a solution of diethylmalonate (9.6 g., 0.075 mole) over a one hour period. After stirring for ten minutes after the evolution of hydrogen has ceased, 6,7-dichloro-2-methyl-2-phenyl-5-trifluoromethylsulfonyloxy-1-indanone (6.64 g., 0.015 mole) dissolved in 50% benzene-dimethylformamide (15 ml.) is added over a 15 minute period and the reaction mixture is stirred at ambient temperature for 18 hours. The solution is poured into water (300 ml.) and concentrated hydrochloric acid (10 ml.), extracted into ether, washed with water, brine and dried over magnesium sulfate. Evaporation of the ether leaves the diethyl indanyl malonate which is hydrolyzed by refluxing for 60 hours in a mixture of acetic acid (70 ml.), water (20 ml.) and concentrated hydrochloric acid (3 ml.) to give (6,7-dichloro-1-oxo-2-methyl-2-phenyl-5-indanyl)acetic acid which melts at 133°–5° C. after crystallization from butyl chloride hexane.

Elemental analysis for $C_{18}H_{14}Cl_2O_3$; Calc.: C, 61.91; H, 4.04; Found: C, 62.37; H, 4.46.

EXAMPLE 2

(2-Cyclopentyl-6,7-dichloro-2-methyl-1-oxo-5-indanyl)acetic acid

Step A: 2-Cyclopentyl-6,7-dichloro-2-methyl-5-trifluoromethylsulfonyloxy-1-indanone A mixture of 6,7-dichloro-2-cyclopentyl-5-hydroxy-2-methyl-1-indanone (20.93 g., 0.07 mole), anhydrous potassium carbonate (25.99 g., 0.188 mole) and dry acetone (350 ml) are stirred at room temperature and treated with trifluoromethane sulfonyl chloride (12.70 g., 0.0754 mmole) in portions. Reaction is complete in about 15 minutes after the completion of the addition. The mixture is filtered and evaporated to dryness. The residue is dissolved in methylene chloride, the solution dried (MgSO₄) and evaporated under vacuum to an oil giving 28.45 g. (94%), Elemental analysis for $C_{16}H_{15}Cl_2F_3O_4S$: Calc.: C, 44.56; H, 3.51; S, 7.43; Found: C, 45.31; H, 3.59; S, 6.96.

Step B: Diethyl (2-cyclopentyl-6,7-dichloro-1-oxo-2-methyl-5-indanyl)malonate

To a stirred suspension of sodium hydride (2.88 g., 120 mmole) in dry dimethylformamide (20 ml), under dry nitrogen and cooled in an ice-bath is added dropwise, a solution of diethyl malonate (19.2 g., 120 mmole) in dimethylformamide (30 ml). The mixture is stirred for one hour in the ice-bath and another hour at room temperature, then is cooled in the ice-bath again and 2-cyclopentyl-6,7-dichloro-2-methyl-5-trifluoromethylsulfonyloxy-1-indanone (12.93 g., 30 mmole) in dimethylformamide (25 ml) is added dropwise over 1-½ hours. The mixture is stirred at room temperature overnight and then poured into a mixture of ice-water (750 ml), methylene chloride (200 ml) and 6 N hydrochloric acid (20 ml). The methylene chloride layer is separated and the aqueous layer extracted with methylene chloride (50 ml). The combined extract is washed with water (500 ml), dried (MgSO₄) and evaporated under vacuum, finally at 70°/0.05 Torr, to give an oil (18.28 g.). This is purified by chromatography on Merck silica gel (1.04 Kg) using 1,1,1-trichloroethane as the solvent. The product is accompanied by some diethyl malonate which is removed at 125°/0.05 Torr to give a viscous oil, 10.25 g. (77%), Elemental analysis for $C_{22}H_{26}Cl_2O_5$: Calc.: C, 59.87; H, 5.94; Cl, 16.06; Found: C, 59.87; H, 6.00; Cl, 15.84.

Step C: 2-Cyclopentyl-6,7-dichloro-2-methyl-1-oxo-5-indanyl acetic acid

A mixture of the diethyl indanyl malonate (5.00 g., 11.34 mmole), 9 N hydrochloric acid (5 ml) and acetic acid (50 ml.) is heated in an oil bath at 125° for 55 hours. The mixture is evaporated under reduced pressure and the syrupy residue is dissolved in methylene chloride (50 ml.). The solution is washed with water (4×25 ml.), dried (MgSO₄) and evaporated under vacuum to a foam. The acid is characterized as the dicyclohexylamine salt, m.p. 167°-167.5° dec. (from acetonitrile).

Elemental analysis for $C_{17}H_{18}Cl_2O_3 \cdot C_{12}H_{23}N$; Calc.: C, 66.66; H, 7.91; N, 2.68; Found: C, 66.70; H, 8.13; N, 2.62.

EXAMPLE 3

By following substantially the procedure described in Example 1, Step A, but substituting for the 6,7-dichloro-5-hydroxy-2-methyl-2-phenyl-1-indanone, an equimolar amount of 7-chloro-2,6-dimethyl-5-hydroxy-2-phenyl-1-indanone and conducting Steps A and B of Example 1 as therein described, there is obtained (7-chloro-2,6-dimethyl-1-oxo-2-phenyl-5-indanyl)acetic acid.

EXAMPLE 4

By following substantially the procedure described in Example 1, Step A, but substituting for the 6,7-dichloro-5-hydroxy-2-methyl-2-phenyl-1-indanone, an equimolar amount of 6,7-dichloro-2-(4-fluorophenyl)-5-hydroxy-2-methyl-1-indanone and conducting Steps A and B of Example 1 as therein described, there is obtained [6,7-dichloro-2-(4-fluorophenyl)-1-oxo-2-methyl-5-indanyl]acetic acid.

EXAMPLE 5

By following substantially the procedure described in Example 1, Step A, but substituting for the 6,7-dichloro-5-hydroxy-2-methyl-2-phenyl-1-indanone, an equimolar amount of 2-(4-chlorophenyl)-6,7-dichloro-5-hydroxy-2-methyl-1-indanone and conducting Steps A and B of Example 1 as therein described, there is obtained [2-(4-chlorophenyl)-6,7-dichloro-1-oxo-2-methyl-5-indanyl]acetic acid.

EXAMPLE 6

By following substantially the procedure described in Example 1, Step A, but substituting for the 6,7-dichloro-5-hydroxy-2-methyl-2-phenyl-1-indanone, an equimolar amount of 6,7-dichloro-5-hydroxy-2-isopropyl-2-methyl-1-indanone and conducting Steps A and B of Example 1 as therein described, there is obtained (6,7-dichloro-2-isopropyl-2methyl-1-oxo-5-indanyl)acetic acid.

EXAMPLE 7

Dry filled capsules containing 100 mg. of active ingredient per capsule

|  | Per Capsule |
|---|---|
| (6,7-dichloro-1-oxo-2-methyl 2-phenyl-5-indanyl)acetic acid | 100 mg. |
| Lactose | 297 mg. |
| Magnesium Stearate | 3 mg. |
| Capsule (Size No. 1) | 400 mg. |

The (6,7-dichloro-1-oxo-2-methyl-2-phenyl-5-indanyl)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds.

What is claimed is:

1. A compound of the formula:

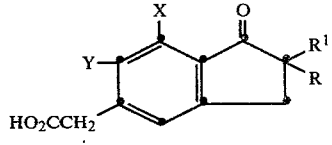

wherein
X and Y are both chloro;
R¹ is lower alkyl;
R is phenyl, and the pharmaceutically acceptable salts thereof.

2. A compound of claim 1 which is (6,7-dichloro-1-oxo-2-methyl-2-phenyl-5-indanyl)acetic acid.

* * * * *